(12) United States Patent
Kinoshita

(10) Patent No.: US 8,747,326 B2
(45) Date of Patent: Jun. 10, 2014

(54) ELECTRONIC SPHYGMOMANOMETER

(75) Inventor: Hiroyuki Kinoshita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 384 days.

(21) Appl. No.: 13/128,437

(22) PCT Filed: Nov. 11, 2009

(86) PCT No.: PCT/JP2009/069190
§ 371 (c)(1),
(2), (4) Date: May 10, 2011

(87) PCT Pub. No.: WO2010/058724
PCT Pub. Date: May 27, 2010

(65) Prior Publication Data
US 2011/0218447 A1 Sep. 8, 2011

(30) Foreign Application Priority Data

Nov. 20, 2008 (JP) ................. 2008-296509

(51) Int. Cl.
*A61B 5/02* (2006.01)
*A61B 5/022* (2006.01)
(52) U.S. Cl.
CPC ............. *A61B 5/022* (2013.01); *A61B 5/02225* (2013.01); *B61B 5/021* (2013.01)
USPC ............ 600/490; 600/494; 600/495; 600/500
(58) Field of Classification Search
CPC ..... A61B 5/021; A61B 5/022; A61B 5/02225
USPC ......................... 600/485, 490–495
See application file for complete search history.

(56) References Cited

U.S. PATENT DOCUMENTS 5,156,158 A * 10/1992 Shirasaki ...................... 600/493
5,522,395 A * 6/1996 Shirasaki et al. ............. 600/495
(Continued)

FOREIGN PATENT DOCUMENTS

JP 57-145640 A 9/1982
JP 61-185250 A 8/1986
(Continued)

OTHER PUBLICATIONS

International Search Report w/translation from PCT/JP2009/069190 dated Dec. 15, 2009 (2 pages).
(Continued)

*Primary Examiner* — Michael Kahelin
*Assistant Examiner* — Tho Tran
(74) *Attorney, Agent, or Firm* — Osha Liang LLP

(57) ABSTRACT

A manual pressurization electronic sphygmomanometer includes a specific component detection unit for detecting a synthetic wave of a manual fluctuation wave and a pressure pulse wave as a specific component from a cuff pressure signal obtained during pressurization; a derivation processing unit for deriving a pressurization target value based on the detection result of the specific component detection unit; and a display unit for notifying to urge pressurization up to the pressurization target value. The derivation processing unit calculates a pulse wave component based on the waveform before and after the specific component and the waveform of the specific component, and determines a value obtained by adding a predetermined value to the systolic blood pressure value estimated based on the amplitude of the pulse wave component as the pressurization target value.

5 Claims, 15 Drawing Sheets

Amplitude = difference of minimal value and next maximal value

Component is recognized as specific component (synthetic wave) if amplitude is lower than constant level, and recognized as manual pressurization component if higher than or equal to constant level

(56) References Cited

U.S. PATENT DOCUMENTS

2006/0064023 A1* 3/2006 Yang et al. ................... 600/490
2007/0185403 A1  8/2007 Yang et al.

FOREIGN PATENT DOCUMENTS

JP    4-261639 A    9/1992
JP    5-42112 A     2/1993

OTHER PUBLICATIONS

Patent Abstracts of Japan Publication No. 05-042112 dated Feb. 23, 1993 (1 page).
Patent Abstracts of Japan Publication No. 04-261639 dated Sep. 17, 1992 (1 page).
Office Action issued in corresponding Russian Application No. 2011124909/14(036788) dated Oct. 16, 2013, and English translation thereof (5 pages).

* cited by examiner

Fig. 3
(A)
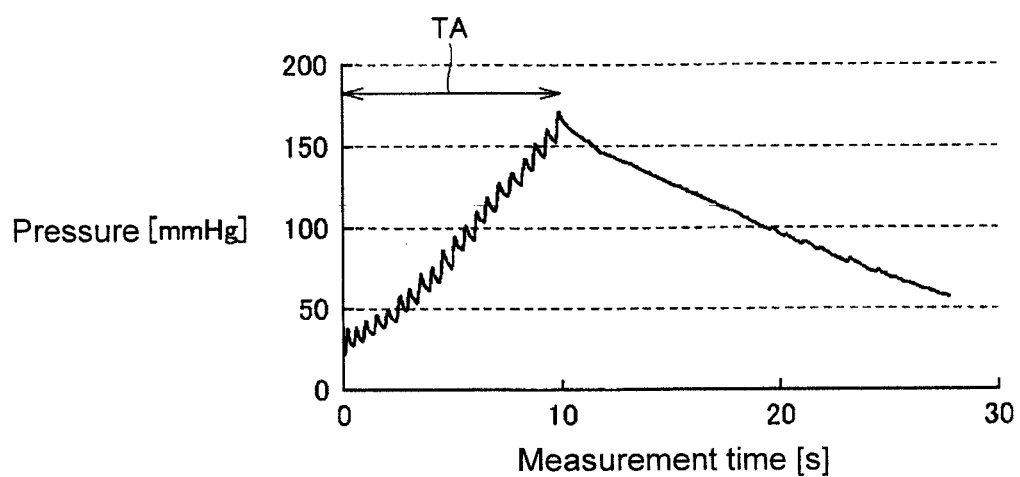
(B)
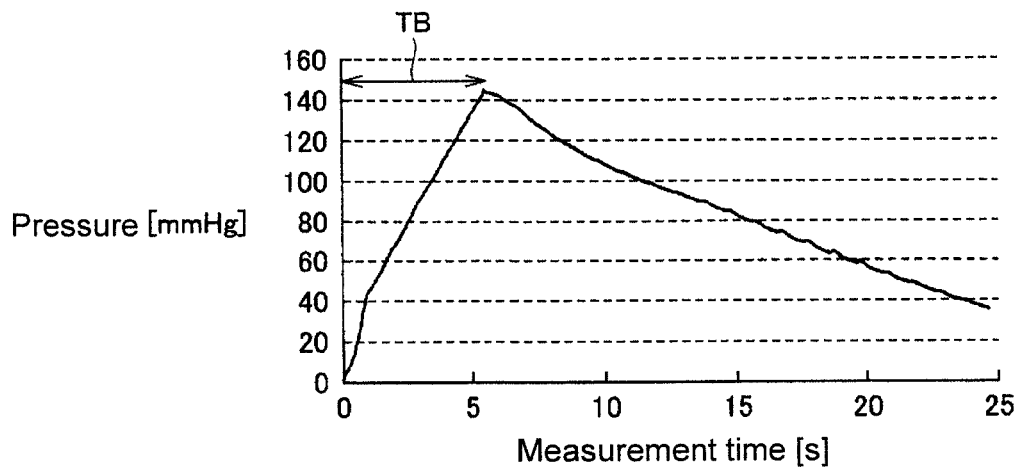

Fig. 4
(A)
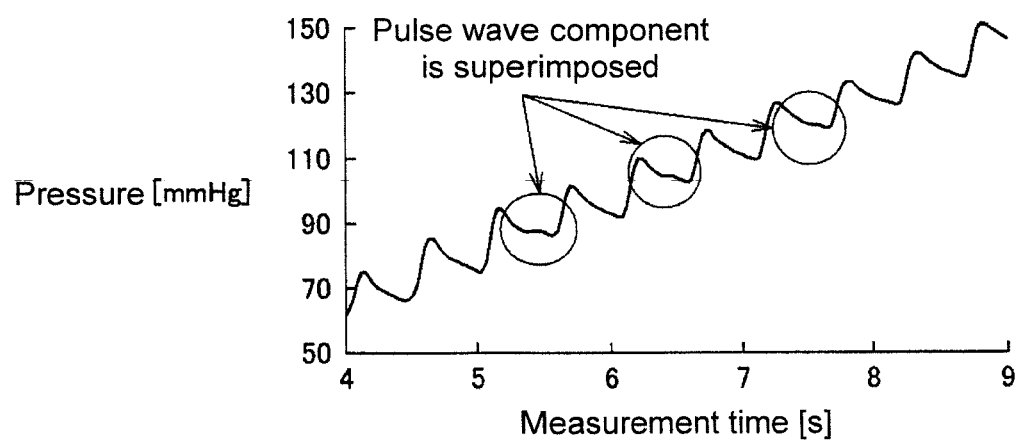
(B)
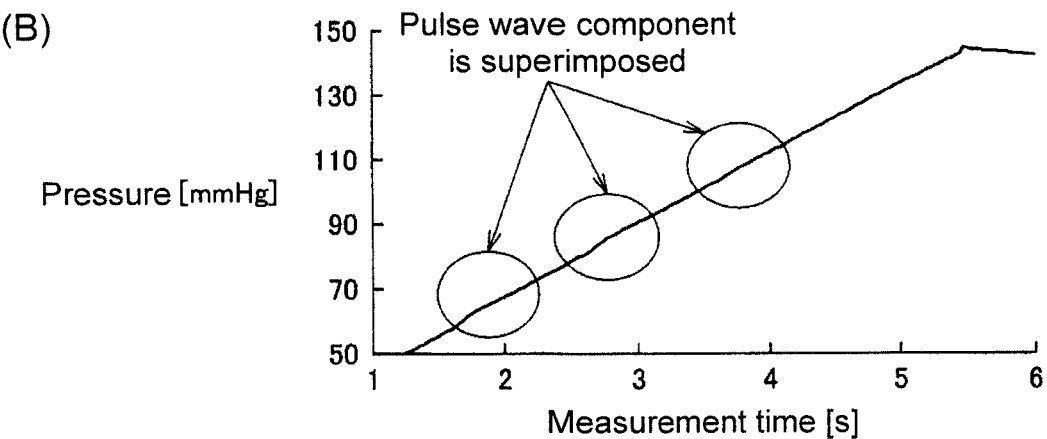

Fig. 9
(A) 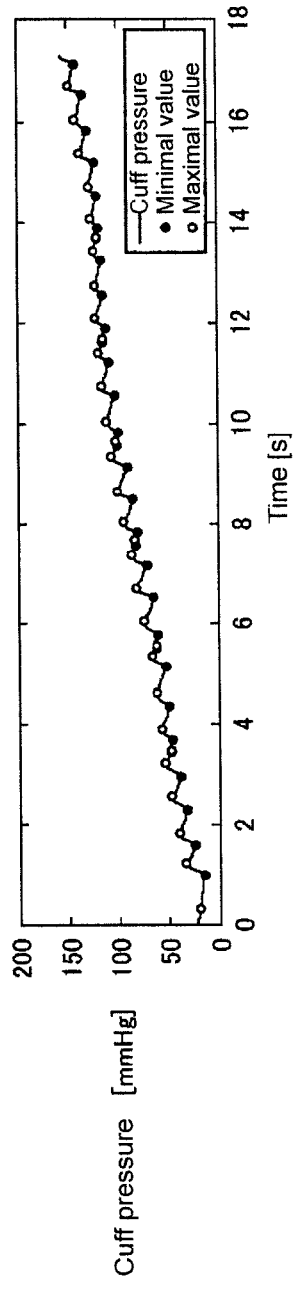
(B) 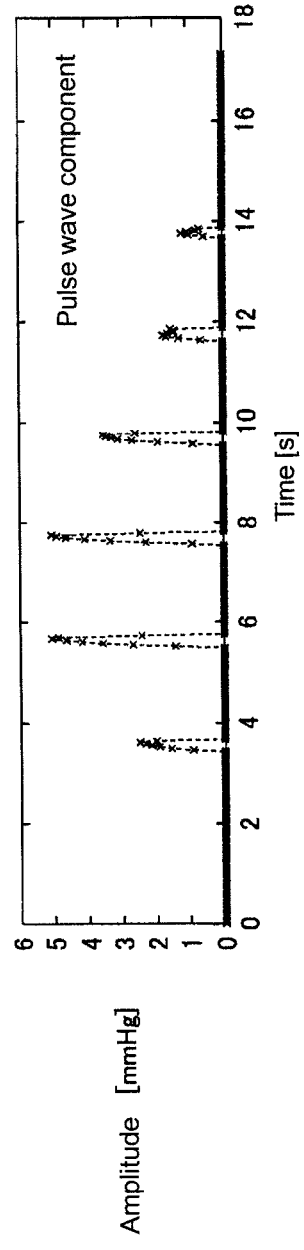
(C) 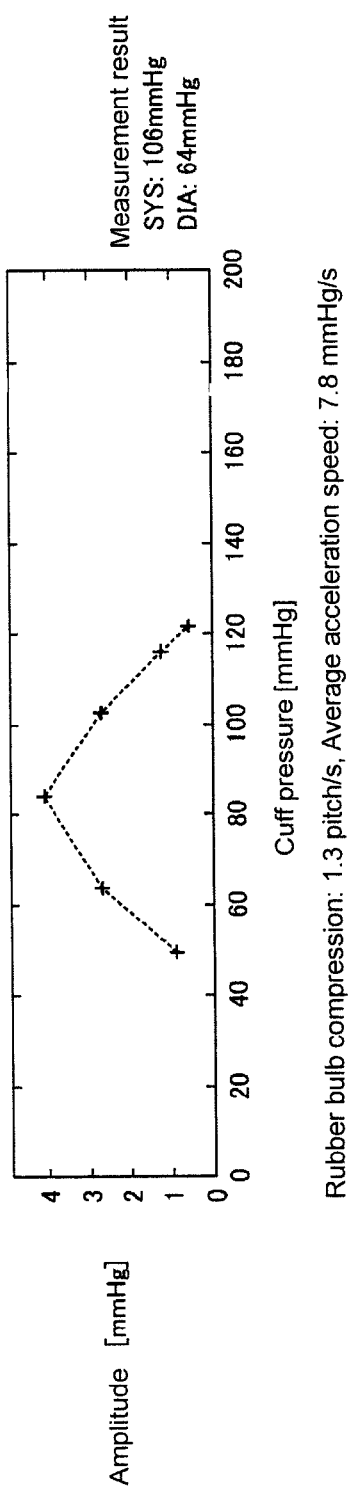

even when the measurement is stopped, whereby the insecurity of the user is alleviated. Furthermore, the blood pressure value can be prevented from being affected by the mental influence.

ELECTRONIC SPHYGMOMANOMETER

TECHNICAL FIELD

The present invention relates to electronic sphygmomanometers, and in particular, to a manual pressurization electronic sphygmomanometer.

BACKGROUND ART

An automatic pressurization sphygmomanometer including a pump and the like, and a manual pressurization sphygmomanometer including a rubber bulb and the like exist from the prior art.

Regarding the automatic pressurization sphygmomanometer, a technique of estimating a systolic blood pressure in a pressurization process, terminating the pressurization at the time point the estimated systolic blood pressure+predetermined value is reached, and transitioning to depressurization exists (Japanese Unexamined Patent Publication No. 4-261639 (Patent Document 1)).

Regarding the manual pressurization sphygmomanometer, on the other hand, the determination of the terminating pressure of the optimum pressurization often relies on the experience of a user. In most current products, instruction is made to pressurize targeting the usual systolic blood pressure value of the person to be measured +30 to 40 mmHg. The user thus does not know up to what pressure value to actually pressurize.

Therefore, regarding the manual pressurization sphygmomanometer, the sphygmomanometer for notifying the user when re-pressurized up to a new pressurization target value, the new pressurization target value being a value obtained by adding a constant value defined in advance to the pressurization value immediately before, when lack of pressurization is detected is proposed (Japanese Unexamined Patent Publication No. 57-145640 (Patent Document 2)).

Patent Document 1: Japanese Unexamined Patent Publication No. 4-261639

Patent Document 2: Japanese Unexamined Patent Publication No. 57-145640

SUMMARY OF INVENTION

In the invention of Japanese Unexamined Patent Publication No. 57-145640 (Patent Document 2), whether or not the pressurization is lacking is detected after pressurization is once terminated, and then the pressurization target of re-step up is notified. Therefore, the user cannot know the pressurization target value unless the pressurization is once stopped.

Therefore, the user cannot determine specifically how much to pressurize in the first pressurizing operation and may feel insecure even if the technique of Japanese Unexamined Patent Publication No. 57-145640 (Patent Document 2) is used. In some cases, such insecurity may affect the blood pressure value. The load of the user when excessively pressurized or when re-pressurization is required due to lack of pressurization is not necessarily small.

Therefore, the technique in which the user can know how much to pressurize during pressurization makes sense from the standpoint of measurement accuracy and usability.

Therefore, one or more embodiments of the present invention provides a manual pressurization electronic sphygmomanometer capable of notifying the user how much to pressurize in a series of pressurizing operations.

One or more embodiments of the present invention are directed to a manual pressurization electronic sphygmomanometer including a cuff to be wrapped around a predetermined body site, a manual pressurization unit for pressurizing pressure in the cuff through a manual operation by a user, a pressure sensor for detecting a cuff pressure signal representing the pressure in the cuff, a specific component detection unit for detecting a synthetic wave of a manual fluctuation wave and a pressure pulse wave as a specific component from the cuff pressure signal obtained during the pressurization, a derivation processing unit for deriving a pressurization target value based on the detection result of the specific component detection unit, and a notification unit for notifying to urge pressurization up to the pressurization target value.

According to one or more embodiments of the present invention, the derivation processing unit includes a first calculating portion for calculating an interpolation curve of the manual fluctuation wave for the portion of the specific component from waveforms before and after the specific component, a second calculating portion for calculating a pulse wave component by subtracting the interpolation curve from the specific component, an estimating portion for estimating a systolic blood pressure value based on an amplitude of the pulse wave component, and a determining portion for determining a value obtained by adding a predetermined value to the estimated systolic blood pressure value as the pressurization target value.

According to one or more embodiments of the present invention, the electronic sphygmomanometer further includes a pressure value detection unit for detecting a current pressure value from the cuff pressure signal obtained during the pressurization, wherein the notification unit displays the current pressure value and the pressurization target value in association to each other.

According to one or more embodiments of the present invention, the notification unit notifies end of pressurization when the current pressure value reaches the pressurization target value.

According to one or more embodiments of the present invention, the derivation processing unit includes a determining portion for determining a value obtained by adding a predetermined value to a pressure value at a time point the specific component is detected as the pressurization target value every time the specific component is detected.

According to one or more embodiments of the present invention, the specific component detection unit detects a pressure fluctuation component in which an amplitude value is smaller than a first threshold value in the cuff pressure signal obtained during the pressurization as the specific component.

According to one or more embodiments of the present invention, the electronic sphygmomanometer further includes a determination unit for determining whether or not a manual amplitude representing an amplitude of the manual fluctuation wave is greater than or equal to a second threshold value, wherein the second threshold value represents a value greater than or equal to the first threshold value. The notification unit further notifies to guide the user so that the manual amplitude becomes greater than or equal to the second threshold value when determined by the determination unit that the manual amplitude is smaller than the second threshold value.

According to one or more embodiments of the present invention, the pressurization can be notified to be carried out up to the pressurization target value even in a manual pressurization sphygmomanometer. Therefore, the user can continue the pressurizing operation with a sense of security until reaching the pressurization target value. Furthermore, excessive compression can be prevented.

BRIEF DESCRIPTION OF THE DRAWINGS

FIGS. 3(A) and 3(B) are diagrams showing the difference in the pressure waveform (shape of cuff pressure signal) caused by the difference in pressurization method.

FIGS. 4(A) and 4(B) are diagrams showing the difference in the pressure waveform at the time of pressurization caused by the difference in pressurization method.

FIGS. 9(A) to 9(C) are diagrams showing examples of the detection of the specific component and the extraction of the pulse wave component when the stroke is small (case of low speed pressurization).

DETAILED DESCRIPTION OF INVENTION

Figure 1:
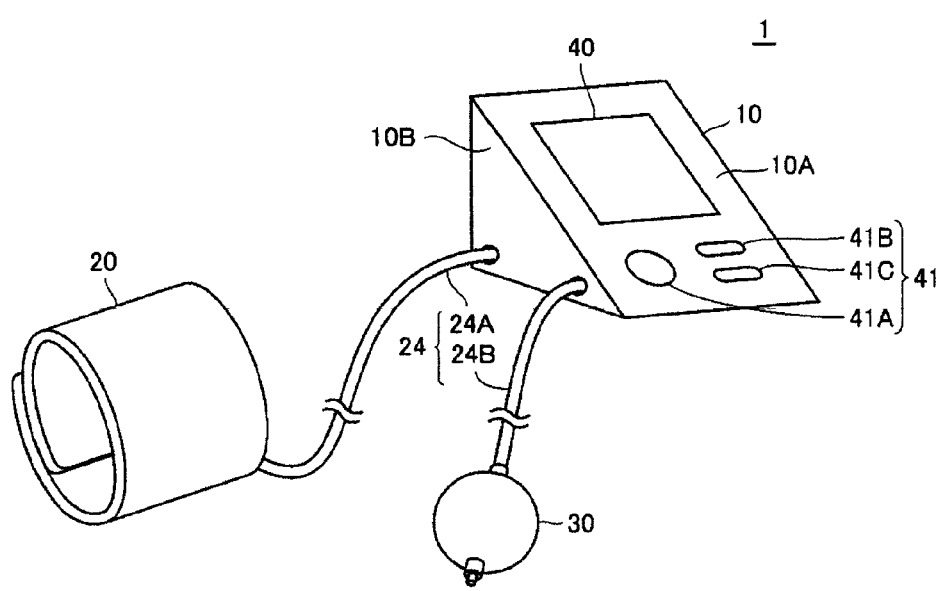
FIG. 1 is a view showing an outer appearance of a sphygmomanometer according to an embodiment of the present invention.

The embodiments of the present invention will be described in detail with reference to the drawings. The same reference numerals are denoted for the same or corresponding portions in the figures, and the description thereof will not be repeated.

(Regarding Outer Appearance)

First, the outer appearance of an electronic sphygmomanometer (hereinafter abbreviated as the "sphygmomanometer") according to the present embodiment will be described with reference to FIG. 1.

FIG. 1 is a view showing an outer appearance of a sphygmomanometer 1 according to an embodiment of the present invention.

With reference to FIG. 1, the sphygmomanometer 1 includes a main body 10, a cuff 20 for attaching to a predetermined body site such as an upper arm of a person to be measured, and an air tube 24A for connecting the main body 10 and the cuff 20. The sphygmomanometer 1 includes a manual pressurization mechanism, and for example, includes a rubber bulb 30 and an air tube 24B for connecting the rubber bulb 30 and the main body 10. The rubber bulb 30 sends air to the cuff 20 through the air tube 24 (24A, 24B) by the compression operation performed by the user.

A display unit 40 for displaying measurement results and the like, and an operation unit 41 for accepting input of instruction from the user (representatively, person to be measured) are arranged on a surface 10A of the main body 10. The operation unit 41 includes a power switch 41A for switching ON/OFF of the power supply, a measurement switch 41B for inputting instruction to start measurement, and a memory switch 41C for inputting instruction to read out and display the past measurement results.

The display unit 40 is configured by a display such as a liquid crystal display.

The air tubes 24A, 24B are connected to a left side surface 10B of the main body 10.

The shape of the main body 10 of the sphygmomanometer 1 is not limited to such an example. The rubber bulb 30 is arranged as a manual pressurization mechanism, but this is not the sole case. Furthermore, the fluid for pressurizing the cuff 20 is not limited to air.

(Regarding Hardware Configuration)

Figure 2:
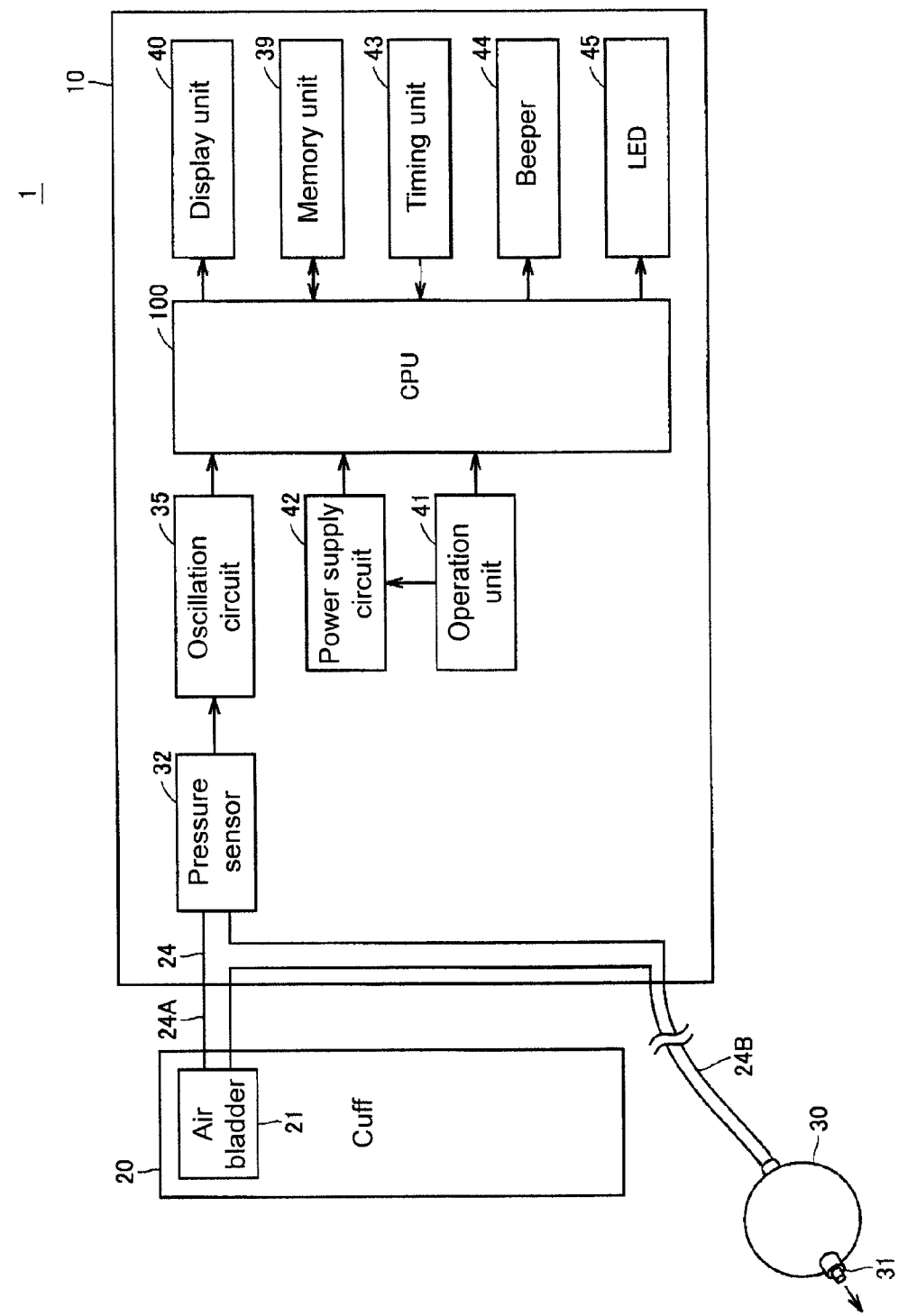
FIG. 2 is a block-diagram showing a hardware configuration of the sphygmomanometer according to the embodiment of the present invention.

FIG. 2 is a block diagram showing a hardware configuration of the sphygmomanometer 1 according to the embodiment of the present invention.

With reference to FIG. 2, the cuff 20 of the sphygmomanometer 1 includes an air bladder 21 in which air is enclosed. The rubber bulb 30 supplies or discharges the air to and from the air bladder 21 through the air tubes 24 (including 24A, 24B). A very small exhaust port 31 for exhausting air at a constant speed is arranged at a predetermined position of the rubber bulb 30. The rubber bulb 30 can rapidly exhaust air when a dedicated switch (not shown) arranged in the operation unit 41 is pushed. The user can supply air to the air bladder 21 by performing compression operation on the rubber bulb 30.

The main body 10 includes a CPU (Central Processing Unit) 100 for intensively controlling and monitoring each unit, a pressure sensor 32, an oscillation circuit 35, a non-volatile memory unit 39, a display unit 40, an operation unit 41, a power supply unit 42, a timing unit 43 for performing the timing operation, a beeper 44 for outputting an alarm sound or a beeping sound, and an LED (Light Emitting Diode) 45 for outputting light.

The pressure sensor 32 is a device for detecting a cuff pressure signal representing the pressure in the air bladder 21 (hereinafter referred to as "cuff pressure"). The capacitance value of the pressure sensor 32 changes by the detected pressure. The oscillation circuit 35 outputs a signal having an oscillating frequency corresponding to the capacitance value of the pressure sensor 32 to the CPU 100. The CPU 100 converts the signal obtained from the oscillation circuit 35 to pressure, and detects the pressure (cuff pressure).

The memory unit 39 stores various types of information such as programs for causing the CPU 100 to perform a predetermined operation and measurement result information.

The power supply unit 42 supplies power to the CPU 100 in response to the instruction to turn ON the power from the operation unit 41.

(Regarding Characteristics of Manual Pressurization Sphygmomanometer)

Prior to describing the function configuration of the sphygmomanometer 1 according to the present embodiment, the characteristics of the manual pressurization sphygmomanometer will be described in comparison with the automatic pressurization sphygmomanometer.

FIGS. 3(A) and 3(B) are diagrams showing the difference in the pressure waveform (shape of cuff pressure signal) caused by the difference in pressurization method, where FIG. 3(A) shows the pressure waveform of the manual pressurization method and FIG. 3(B) shows the pressure waveform of the automatic pressurization method.

With reference to FIG. 3(A), in the manual pressurization sphygmomanometer, the cuff is pressurized when the user (representatively, person to be measured) manually operates (compression operation) the rubber bulb over a plurality of times. A large pressure fluctuation involved in the manual operation thus appears in the pressure waveform at the time of pressurization. The wave indicating the pressure fluctuation generated with the manual operation, that is, the pressure fluctuation wave caused by the manual operation is referred to as a "manual fluctuation wave".

With reference to FIG. 3(B), on the other hand, a large pressure fluctuation as appeared in the case of manual operation does not exist in the automatic pressurization method. Therefore, in the case of the automatic pressurization method, the component of the pressure pulse wave (hereinafter referred to as a "pulse wave component") can be easily captured from the pressure waveform at the time of pressurization. The "pressure pulse wave" is the pressure fluctuation wave representing the fluctuation in the intravascular capacity involved in the pulsation of the heart.

The details of the pressure waveform at the time of pressurization will be further described with reference to FIGS. 4(A) and 4(B). FIGS. 4(A) and 4(B) are diagrams showing the difference in the pressure waveform at the time of pressurization caused by the difference in pressurization method, where FIG. 4(A) displays the pressure waveform in a period TA of FIG. 3(A) in an enlarged manner and FIG. 4(B) displays the pressure waveform in a period TB of FIG. 3(B) in an enlarged manner.

With reference to FIG. 4(B), the pulse wave component superimposed on the cuff pressure signal can be easily extracted because the pressurization can be carried out at substantially a constant speed by using the pump and the like in the case of the automatic pressurization method. That is, the pressure fluctuation component appearing in the pressure waveform can all be recognized as the pressure pulse wave. In the present embodiment, the "pressure fluctuation component" represents the waveform from the minimal value to the next minimal value when the difference between the minimal value and the next maximal value of the pressure waveform is defined as an "amplitude".

With reference to FIG. 4(A), on the other hand, the pressure fluctuation component appearing in the pressure waveform is mainly configured by the manual fluctuation wave in the case of the manual pressurization method. However, the speed at the time of releasing compression (lowering of cuff pressure) is slower (constant) than the speed at the time of compression (increasing of cuff pressure). Therefore, the pulse wave component may be superimposed on the cuff pressure signal at the time of releasing compression. Therefore, a plurality of pressure fluctuation components (waveforms) appearing in the pressure waveform in the case of the manual pressurization method includes the component configured with only the manual fluctuation wave (hereinafter referred to as a "manual pressurization component") and the synthetic wave of the manual fluctuation wave and the pressure pulse wave (hereinafter referred to as a "specific component").

The sphygmomanometer 1 according to the present embodiment derives the pressurization target value by detecting the specific component from the pressure waveform (cuff pressure signal) during pressurization. A specific function configuration example of the sphygmomanometer 1 according to the present embodiment will be described below.

(Regarding Function Configuration)

Figure 5:
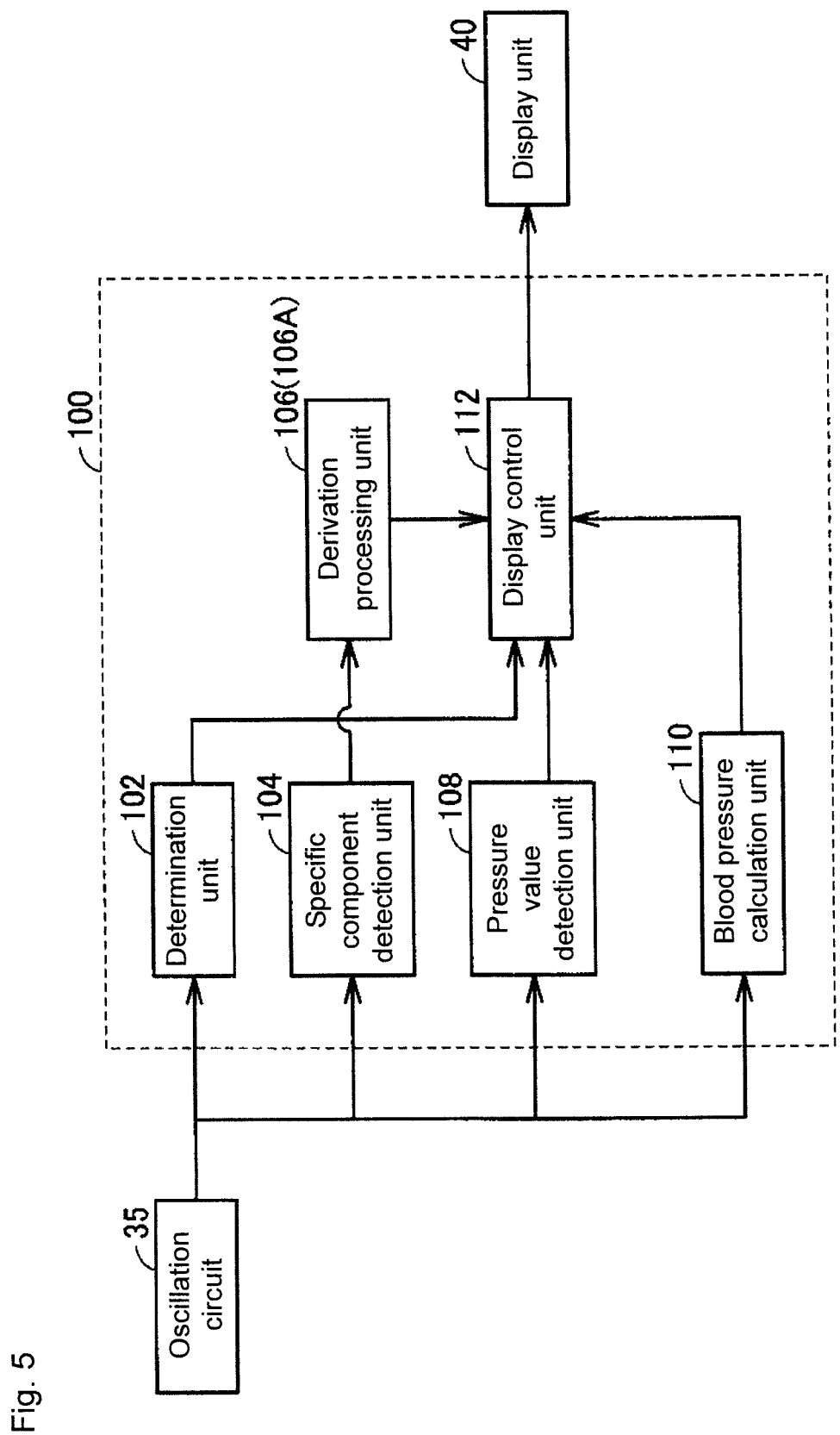
FIG. 5 is a function block diagram showing a function configuration of the sphygmomanometer according to the embodiment of the present invention.

FIG. 5 is a function block diagram showing the function configuration of the sphygmomanometer 1 according to the embodiment of the present invention.

With reference to FIG. 5, the CPU 100 of the sphygmomanometer 1 includes a determination unit 102, a specific component detection unit 104, a derivation processing unit 106, a pressure value detection unit 108, a blood pressure calculation unit 110, and a display control unit 112 for the functions. In FIG. 5, only the peripheral hardware that directly exchanges signals with each unit of the CPU 100 are shown for the sake of simplifying the description.

The specific component detection unit 104 is connected to the oscillation circuit 35, and detects the specific component, that is, the synthetic wave of the manual fluctuation wave and the pressure pulse wave from the pressure waveform (cuff pressure signal) during the pressurization.

Figure 6:
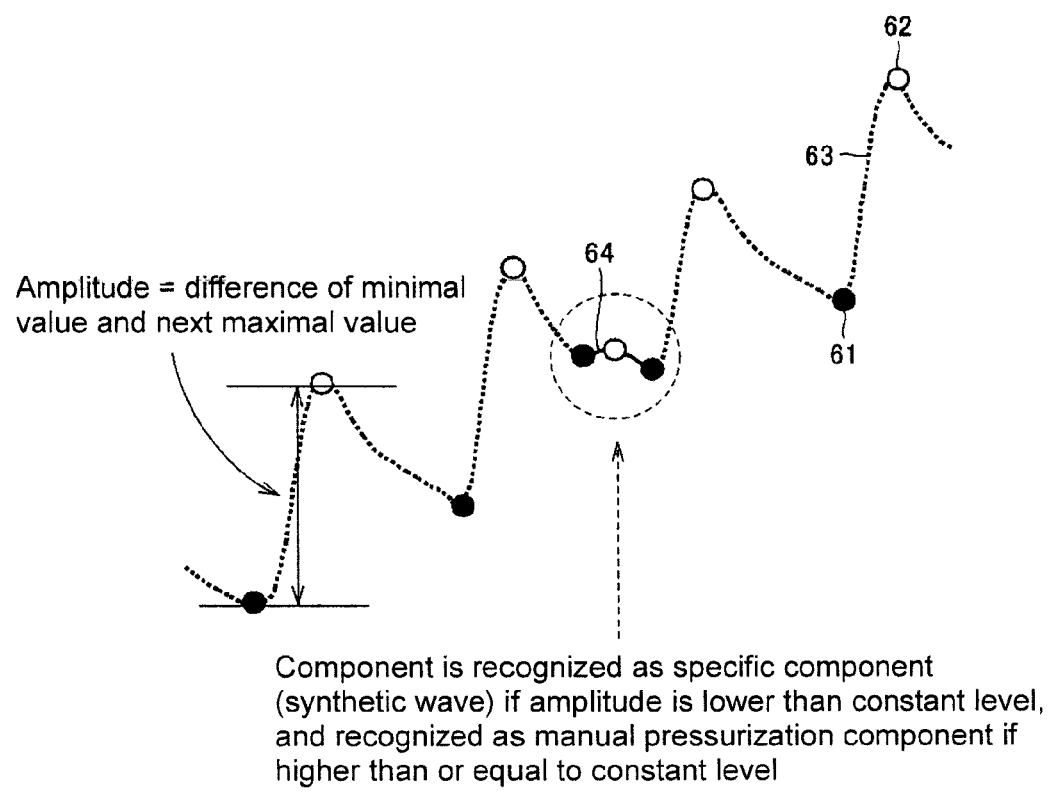
FIG. 6 is a diagram showing a method of detecting a specific component (synthetic wave of manual fluctuation wave and pressure pulse wave) according to the embodiment of the present invention.

FIG. 6 is a diagram showing a method of detecting the specific component.

With reference to FIG. 6, when the difference of a minimal value 61 and a maximal value 62 is expressed as an amplitude, as described above, out of a plurality of pressure fluctuation components, the component in which the amplitude is lower than a predetermined constant level can be recognized as the specific component and the component in which the amplitude is higher than or equal to the constant level can be recognized as the manual pressurization component.

Therefore, the specific component detection unit 104 detects the pressure fluctuation component in which the amplitude is smaller than a predetermined threshold value Va (constant level) as the specific component. In the example of FIG. 6, a curve 63 represents the manual pressurization component and a curve 64 represents the specific component.

Thus, the amplitude of the manual fluctuation wave (hereinafter referred to as the "manual amplitude") needs to be greater than or equal to the threshold value Va in order to separate (classify) the pressure waveform into the specific component and the manual pressurization component according to whether or not greater than or equal to the threshold value Va. Therefore, if the amplitude of greater than or equal to the threshold value Va cannot be detected, the notification (guide process) of urging appropriate pressurization is performed according to one or more embodiments of the present invention. Such a guide process is executed by the determination unit 102 and the display control unit 112.

The necessity to guide the user so that the manual amplitude becomes greater than or equal to the threshold value Va (i.e., so that one stroke of the manual operation becomes large) will be more specifically described below.

Figure 7:
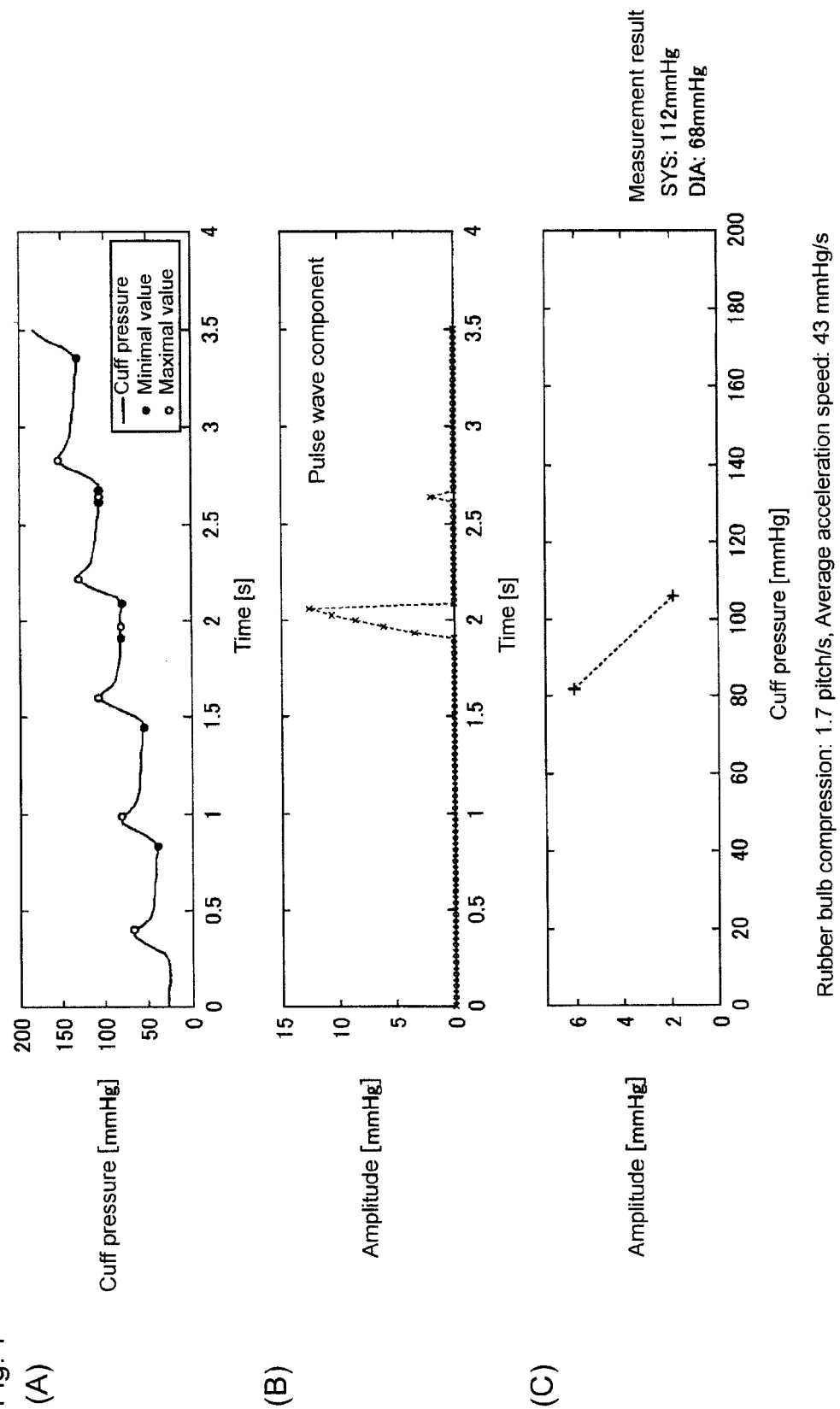
FIGS. 7(A) to 7(C) are diagrams showing examples of the detection of the specific component and the extraction of the pulse wave component when the stroke is large (case of rapid pressurization).
Figure 8:
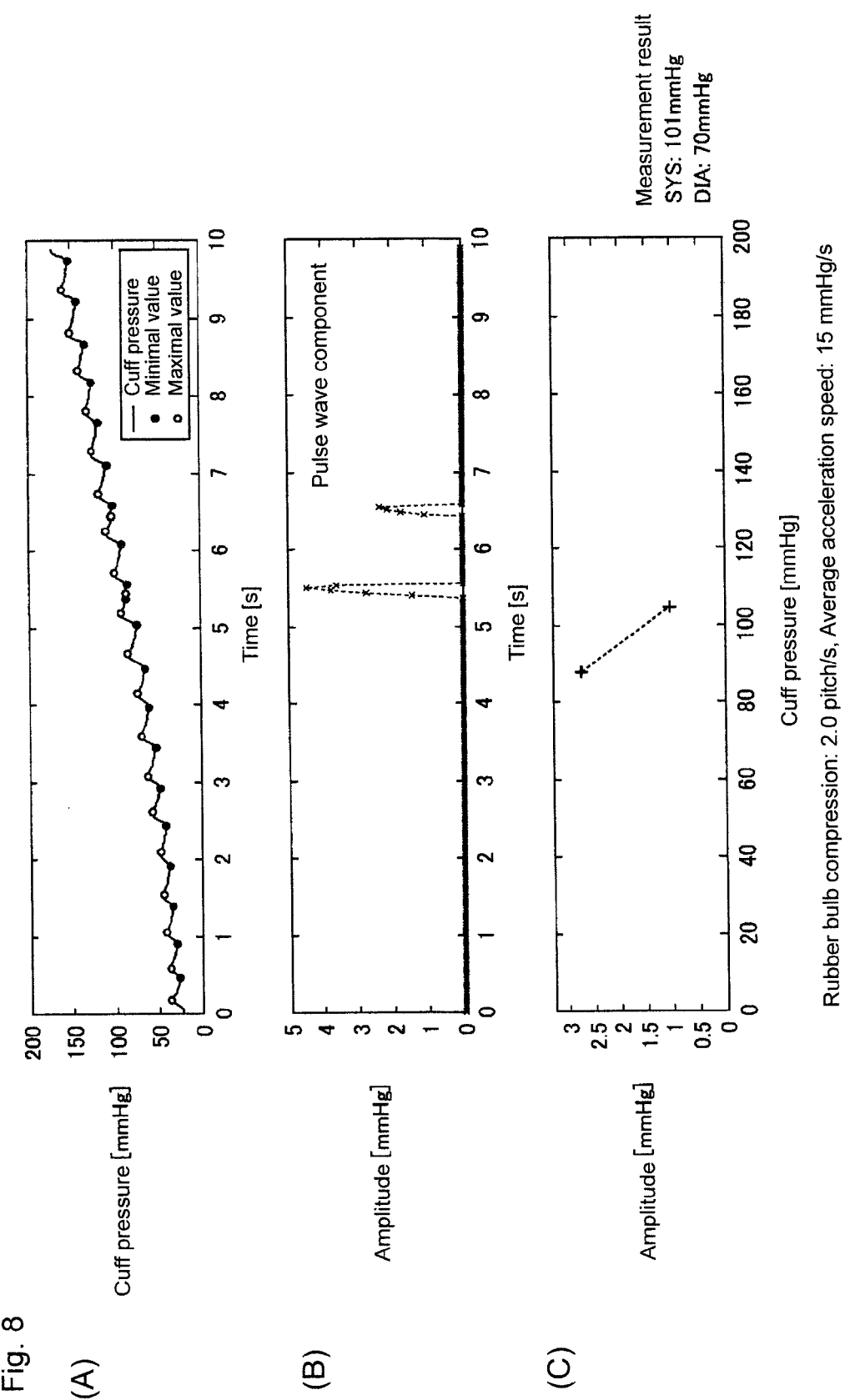
FIGS. 8(A) to 8(C) are diagrams showing examples of the detection of the specific component and the extraction of the pulse wave component when the stroke is normal (case of general speed).
Figure 10:
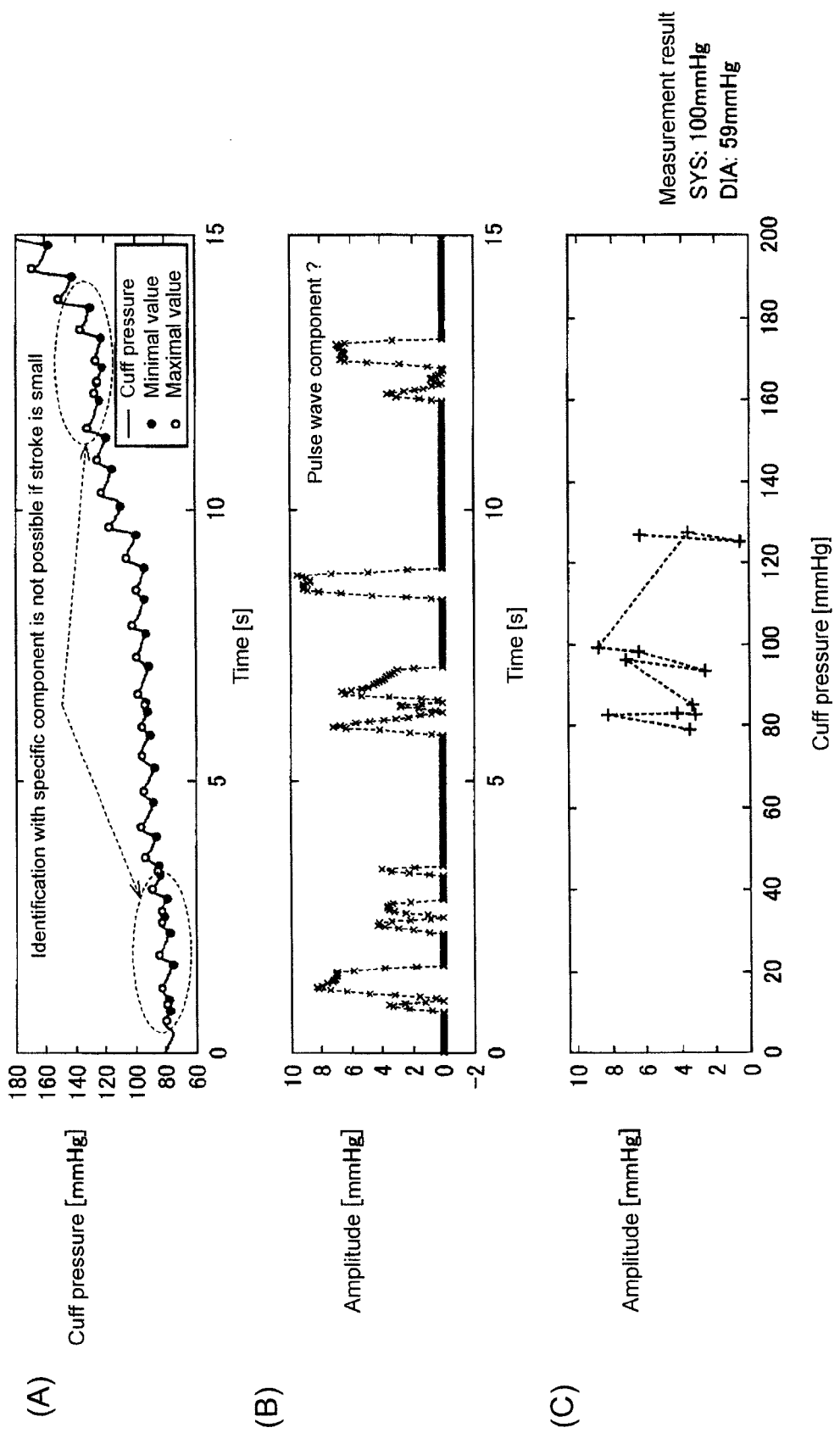
FIGS. 10(A) to 10(C) are diagrams showing examples of the detection of the specific component and the extraction of the pulse wave component when the magnitude of the stroke is irregular.

FIGS. 7(A) to 7(C) are diagrams showing examples of the detection of the specific component and the extraction of the pulse wave component when the stroke is large (case of rapid pressurization). FIGS. 8(A) to 8(C) are diagrams showing examples of the detection of the specific component and the extraction of the pulse wave component when the stroke is normal (in the case of general speed). FIGS. 9(A) to 9(C) are diagrams showing examples of the detection of the specific component and the extraction of the pulse wave component when the stroke is small (case of low speed pressurization). FIGS. 10(A) to 10(C) are diagrams showing examples of the detection of the specific component and the extraction of the pulse wave component when the magnitude of the stroke is irregular.

With reference to FIGS. 7(A) to 7(C), FIG. 7(A) shows the cuff pressure signal in a case where the rubber bulb compression is 1.7 pitch/s and the average acceleration speed is 43 mmHg/s along the time axis for when the stroke is large by way of example. Because the value of the manual amplitude is large if the stroke of the compressing operation is large, the difference between the manual amplitude and the actual pulse wave amplitude (amplitude of pressure pulse wave) is very large. Therefore, in such a case, the specific component having a small amplitude can be detected at high accuracy. FIG. 7(B) shows the waveform (vertical axis: amplitude) of the pulse wave component extracted from the detected specific component along the time axis same as the graph of FIG. 7(A). This is the same for the following graphs. The specific method of extracting (calculating) the pulse wave component from the specific component will be hereinafter described.

With reference to FIGS. 8(A) to 8(C), FIG. 8(A) shows the cuff pressure signal in a case where the rubber bulb compression is 2.0 pitch/s and the average acceleration speed is 15 mmHg/s along the time axis for when the stroke is normal by way of example. The difference between the manual amplitude and the actual pulse wave amplitude is relatively large even if the stroke of the compressing operation is normal. Therefore, in such a case as well, the specific component having a small amplitude can be detected at satisfactory accuracy.

With reference to FIGS. 9(A) to 9(C), FIG. 9(A) shows the cuff pressure signal in a case where the rubber bulb compression is 1.3 pitch/s and the average acceleration speed is 7.8 mmHg/s along the time axis for when the stroke is small by way of example. Because the value of the manual amplitude is small compared to the above examples if the stroke of the compressing operation is small, the difference between the manual amplitude and the actual pulse wave amplitude is also small. Therefore, in such a case, the manual pressurization component may be mistakenly recognized as a specific component.

With reference to FIGS. 10(A) to 10(C), similarly, the manual pressurization component and the specific component are impossible to identify at areas where the stroke is extremely small when the magnitude of the stroke is irregular. In such a case, assumption is made that the pressure fluctuation component smaller than the threshold value Va is detected, and an interpolation curve is calculated for the relevant portion (specifically described later). Then, whether the calculated curve actually represents the pulse wave component cannot be distinguished.

In the graphs of FIGS. 7(C), 8(C), 9(C), and 10(C), the cuff pressure is shown on the horizontal axis and the amplitude value of the extracted pulse wave component is shown on the vertical axis. The systolic blood pressure (SYS) and the diastolic blood pressure (DIA) estimated by applying a predetermined algorithm on the amplitude value of the extracted pulse wave component are shown on the right of such graphs.

Therefore, the manual amplitude needs to be at least greater than or equal to the threshold value Va in order to satisfactorily detect the specific component without mistaken recognition. The threshold value Va merely needs to be a value greater than the maximum value of the pulse wave amplitude obtained through clinical experiments and the like. For example, assume that the maximum value of the pulse wave amplitude obtained in the experiment is 1.5 mmHg and the minimum value of the manual amplitude is 6.0 mmHg. The average value and the standard deviation of the pulse wave amplitude are 0.34 mmHg and 0.3 mmHg, respectively, and the average value and the standard deviation of the manual amplitude are 16.16 mmHg and 7.12 mmHg, respectively. The threshold value Va is then defined in advance as 2.0 mmHg, for example of 1.5 to 6.0 mmHg. The threshold value Va is set to such value because the standard deviation of the pulse wave amplitude is small.

According to one or more embodiments of the present invention, in order to more reliably avoid the manual pressurization component from being mistakenly recognized as the specific component, the threshold value urging an appropriate compression stroke is made larger than the threshold value Va used for the detection of the specific component. That is, the threshold value Vb is a value greater than the threshold value Va, where "Vb" is a threshold value urging an appropriate compression stroke. Therefore, the threshold value Vb may be defined in advance as 4.0 mmHg of 1.5 to 6.0 mmHg in the above example. However, it is not restrictive, and the threshold value Va and the threshold value Vb may be the same value.

The threshold value Vb may be a value greater than or equal to a minimum value (6.0 mmHg in the above example) of the manual amplitude obtained by experiment. However, if the value is set to be too large, the user with weak gripping power may be constantly notified to obtain a large stroke, and hence, a value as small as possible is to be set.

Figure 11:
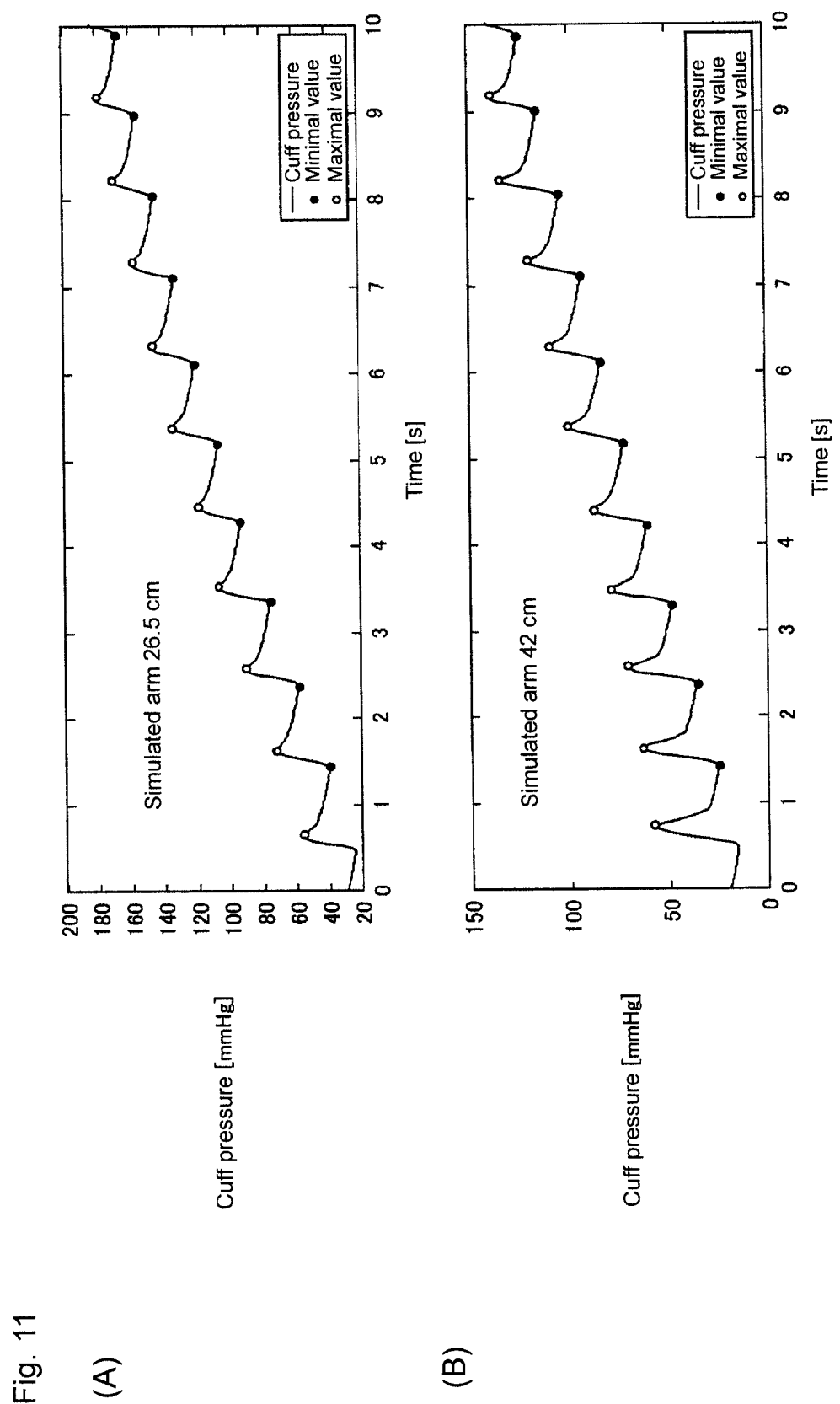
FIGS. 11(A) and 11(B) are diagrams showing the difference in pressure waveform caused by the difference in arm periphery.

If the thickness of the arm of the person to be measured differs, the acceleration speed differs even if the rubber bulb 30 is compressing operated in the same way. FIGS. 11(A) and 11(B) show the difference in the pressure waveform caused by the difference in arm periphery. FIG. 11(A) shows the pressure waveform of the person to be measured having an arm of normal thickness (arm periphery of 26.5 cm), and FIG. 11(B) shows the pressure waveform of the person to be measured having a thick arm (arm periphery of 42 cm). As shown in FIGS. 11(A) and 11(B), the acceleration speed changes if the thickness of the arm of the person to be measured differs, but the specific component can be accurately detected regardless of the thickness of the arm by setting the threshold value Vb to an appropriate value.

With reference again to FIG. 5, the determination unit 102 is connected to the oscillation circuit 35 to determine whether or not the manual amplitude is greater than or equal to the threshold value Vb.

If the manual amplitude is smaller than the threshold value Vb, the information notifying the same is output to the display control unit 112. The display control unit 112 performs the display to guide the user so that the manual amplitude becomes greater than or equal to the threshold value Vb (make the stroke of the compressing operation larger) based on the information from the determination unit 102.

The derivation processing unit 106 derives the pressurization target value based on the detection result by the specific component detection unit 104. In the present embodiment, the derivation processing unit 106 estimates the systolic blood pressure value by extracting the pulse wave component from the specific component. The value obtained by adding a predetermined value (e.g., 40 mmHg) to the systolic blood pressure is determined as the pressurization target value. The specific processes to be executed by the derivation processing unit 106 will be described later.

The pressure value detection unit 108 is connected to the oscillation circuit 35 to detect the current pressure value from the cuff pressure signal obtained during pressurization. The method of detecting the current pressure value is not particularly limited because the detection and display of the current pressure value have been carried out during the manual pressurization from the prior art. Specifically, the average pressure value (average of minimal value and maximal value) of each pressure fluctuation component may be detected as the current pressure value.

The blood pressure calculation unit 110 is connected to the oscillation circuit 35 to calculate the blood pressure (e.g., systolic blood pressure, diastolic blood pressure) from the cuff pressure signal obtained during depressurization at a constant speed. The processes by the blood pressure calculation unit 110 may be realized by the oscillometric method, and the like.

The display control unit 112 displays various types of information on the display unit 40 according to the signal from each unit.

The operation of each function block may be realized by executing the software stored in the memory unit 39, or at least one may be realized by hardware.

<Regarding Operation>

Figure 12:
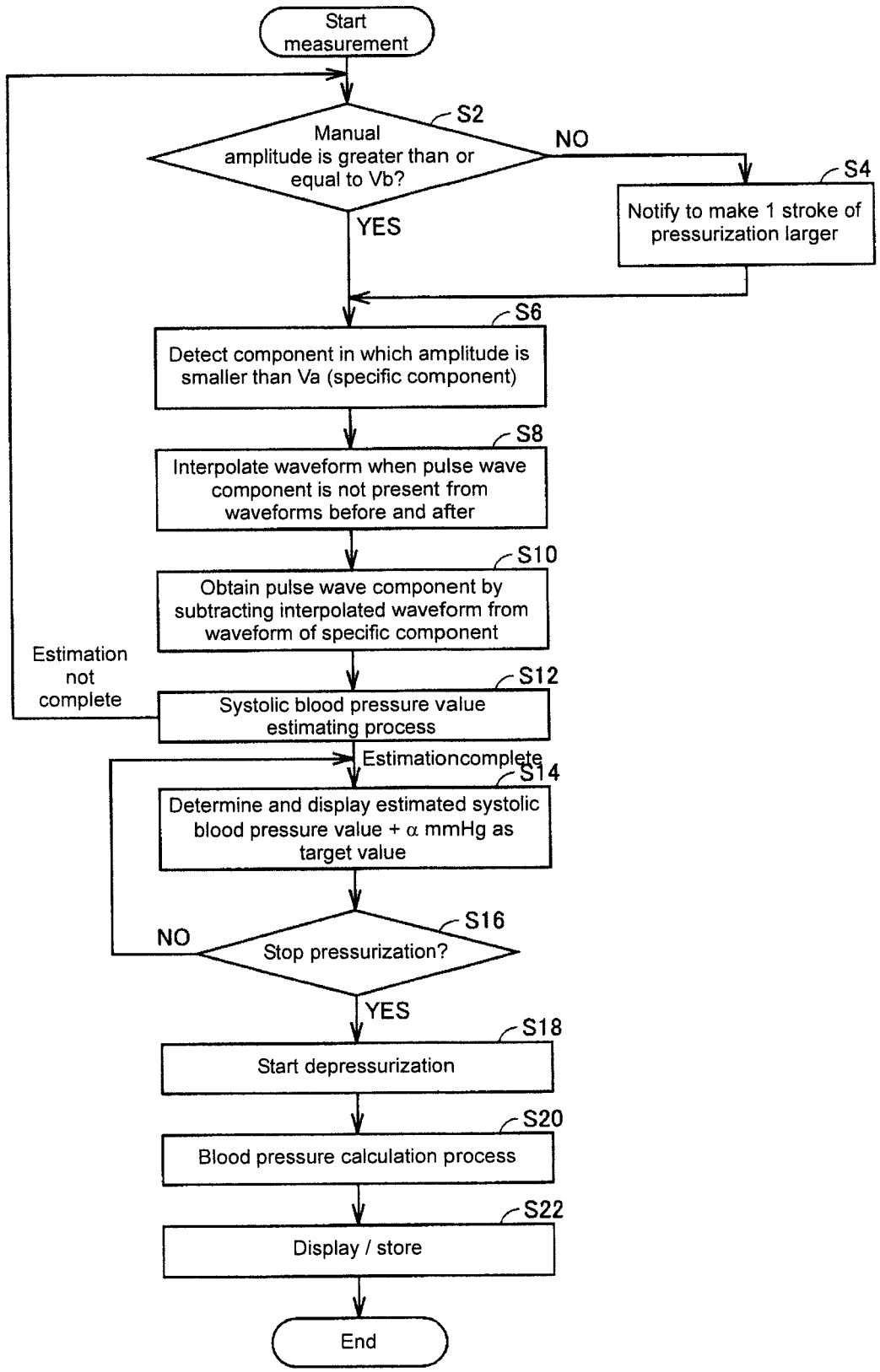
FIG. 12 is a flowchart showing the flow of a blood pressure measurement process according to the embodiment of the present invention.

FIG. 12 is a flowchart showing the flow of a blood pressure measurement process according to the embodiment of the present invention. The process shown in the flowchart of FIG. 12 is stored in the memory unit 39 as a program in advance, where the function of the blood pressure measurement process is realized when the CPU 100 reads out and executes such a program.

The blood pressure measurement process described below starts when the power switch 41A and the measurement switch 41B are pushed, and the user starts the compressing operation of the rubber bulb 30. When the power switch 41A is pushed, the CPU 100 initializes the work memory and performs the 0 mmHg adjustment of the pressure sensor 32.

The process by the pressure value detection unit 108 is assumed to be carried out in parallel to the blood pressure measurement process. Thus, the current pressure value detected by the pressure value detection unit 108 during the blood pressure measurement process is displayed in a predetermined display region of the display unit 40 by the display control unit 112.

With reference to FIG. 12, when the pressurizing operation by the user starts, the determination unit 102 determines whether or not the amplitude of the manual pressurization component of the pressure waveform, that is, the manual amplitude is greater than or equal to the threshold value Vb (step S2). The pulse component is not superimposed on the cuff pressure signal immediately after the start of the blood pressure measurement process because the measurement site is not yet compressed by the cuff 20. The pressure fluctuation component detected immediately after the start is thus determined as the manual pressurization component.

The process proceeds to step S6 if the manual amplitude is greater than or equal to the threshold value Vb (YES in step S2).

If the manual amplitude is smaller than the threshold value Vb (NO in step S2), the display control unit 112 notifies to make the stroke of pressurization larger (step S4). The user is then guided to make the stroke of pressurization larger (increase the acceleration speed). After the manual operation is carried out over a couple of times, the pressure fluctuation component may be a specific component (synthetic wave of manual fluctuation wave and pressure pulse wave). Thus, according to one or more embodiments of the present invention, the process of step S4 is carried out only when the case in which the amplitude is smaller than the threshold value Vb is successively detected for a plurality of times (e.g., two times).

The process proceeds to step S6 after the process of step S4 is finished.

In step S6, the specific component detection unit 104 detects the pressure fluctuation component in which amplitude is smaller than the threshold value Va as the specific component. According to one or more embodiments of the present invention, this process is carried out only when the case in which the amplitude of the pressure fluctuation component is greater than or equal to the threshold value Vb is detected at least once in step S2. The manual pressurization component may be mistakenly recognized as the specific component if the relevant process is carried out with a small stroke of pressurization.

After the specific component is detected, the derivation processing unit 106 interpolates the waveform in a case where the pulse wave component is not present for the portion of the specific component from the waveforms before and after (step S8). In other words, the interpolation curve of the manual fluctuation wave is calculated for the portion of the specific component. The process of step S8 will be described in detail with reference to FIG. 13.

Figure 13:
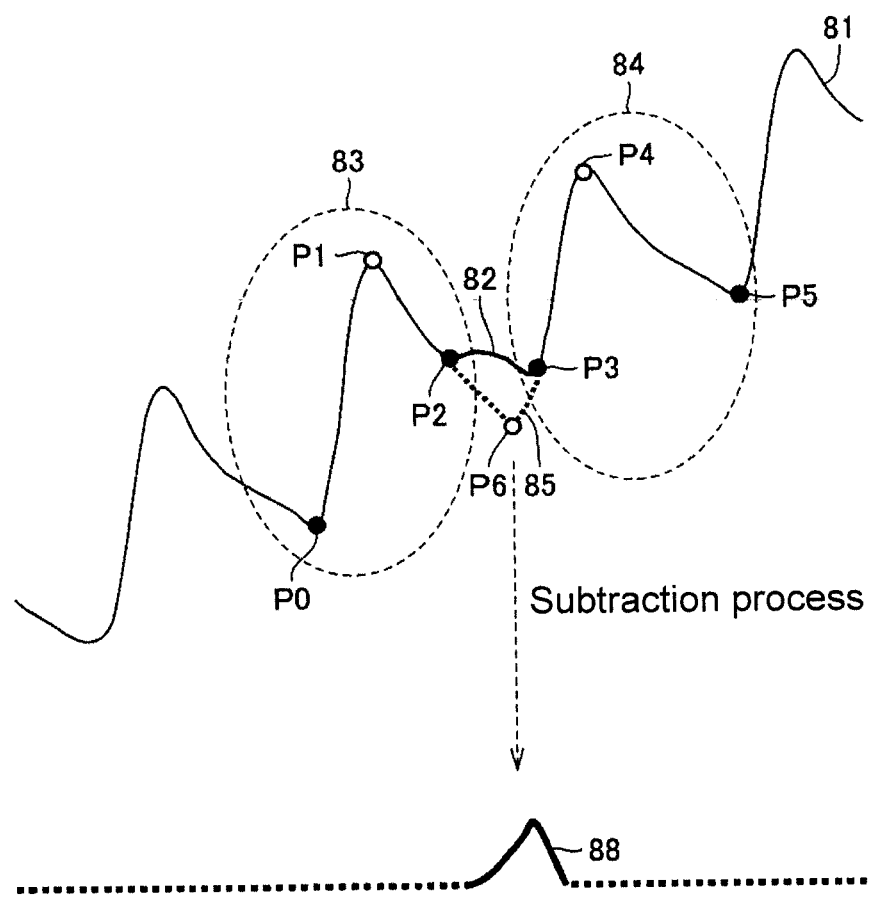
FIG. 13 is a diagram showing a method of extracting the pulse wave component during the manual pressurization in the embodiment of the present invention.

FIG. 13 is a diagram showing a method of extracting the pulse wave component during the manual pressurization.

With reference to FIG. 13, the pressure waveform during the pressurization is configured by a manual pressurization component 81 and a specific component 82. The specific component 82 shows the wave (pressure fluctuation component) from the minimal point P2 to the next minimal point P3. The pressure fluctuation component 83 immediately before the specific component 82 shows the wave from the minimal point P0 to the next minimal point P2. The pressure fluctuation component 84 immediately after the specific component 82 shows the wave from the minimal point P3 to the next minimal point P5.

After the specific component is detected, the manual fluctuation wave is estimated by the interpolation process for the portion for the specific component from the waveforms before and after, that is, the pressure fluctuation components (manual pressurization components) 83, 84.

More specifically, a point P6 where a line passing the maximal point P1 of the pressure fluctuation component 83 and a minimal point (rising point) P2 of the specific component 82, and a line passing the minimal point (rising point) P3 and a maximal point P4 of the pressure fluctuation component 84 intersect is obtained. The interpolation curve 85 is calculated by assuming such a point P6 as the minimal point of the manual fluctuation wave.

Thereafter, the derivation processing unit 106 calculates the pulse wave component by subtracting the interpolated waveform from the waveform of the specific component (step S10). Specifically, with reference again to FIG. 13, the pulse wave component 88 is extracted by subtracting the interpolation curve 85 from the specific component 82.

The derivation processing unit 106 assumes the calculated pulse wave component as the pulse wave waveform for one pulse. The systolic blood pressure estimating process is then executed based on the amplitude of the calculated pulse wave component through the method existing from the prior art (step S12). Specifically, for example, the systolic blood pressure can be estimated based on the change of the pulse wave amplitude using the technique of Japanese Unexamined Patent Publication No. 4-261639 (Patent Document 1). If the pulse wave is detected only for one pulse, the systolic blood pressure can be estimated with the pressure value at the time of detection+predetermined value as the systolic blood pressure.

The process returns to step S2, and the above process is repeated if the estimation of the systolic blood pressure is not completed. The process proceeds to step S14 if the systolic blood pressure estimating process is completed.

In step S14, the derivation processing unit 106 determines the value in which a predetermined value α (e.g., 40 mmHg) is added to the estimated systolic blood pressure value as the pressurization target value. The display control unit 112 displays the determined pressurization target value in a predetermined display region of the display unit 40. As described above, the pressurization target value and the current pressure value are displayed in association with each other because the current pressure value is displayed in a different display region of the display unit 40. Therefore, the user can grasp how much longer the pressurizing operation is to be carried out.

The display of the pressurization target value is executed until the pressurization is stopped (NO in step S16). When the pressurization is stopped (YES in step S16), the depressurization is started (step S18). The blood pressure calculation unit 110 then calculates the systolic blood pressure and the diastolic blood pressure (step S20).

Lastly, the calculated systolic blood pressure and the diastolic blood pressure are displayed on the display unit 116 as measurement results, and stored in the memory unit 39 (step S22).

The blood pressure measurement process is terminated in such a manner.

Therefore, according to the present embodiment, the systolic blood pressure can be estimated even during pressurization by hand. Therefore, the same value as the pressure value (estimated systolic blood pressure value+α) at the end of pressurization in the automatic pressurization method can be displayed as the pressurization target value. As a result, the user can grasp specifically up to what mmHg to pressurize in a series of pressurizing operations, so that lack of pressurization can be avoided and excessive compression can be prevented.

Furthermore, the user can resolve the psychological stress (insecurity) of how much to pressurize. Therefore, the error can be prevented from occurring in the blood pressure value due to psychological stress. The measurement accuracy thus can be enhanced as a result.

(Display Example)

Figure 14:
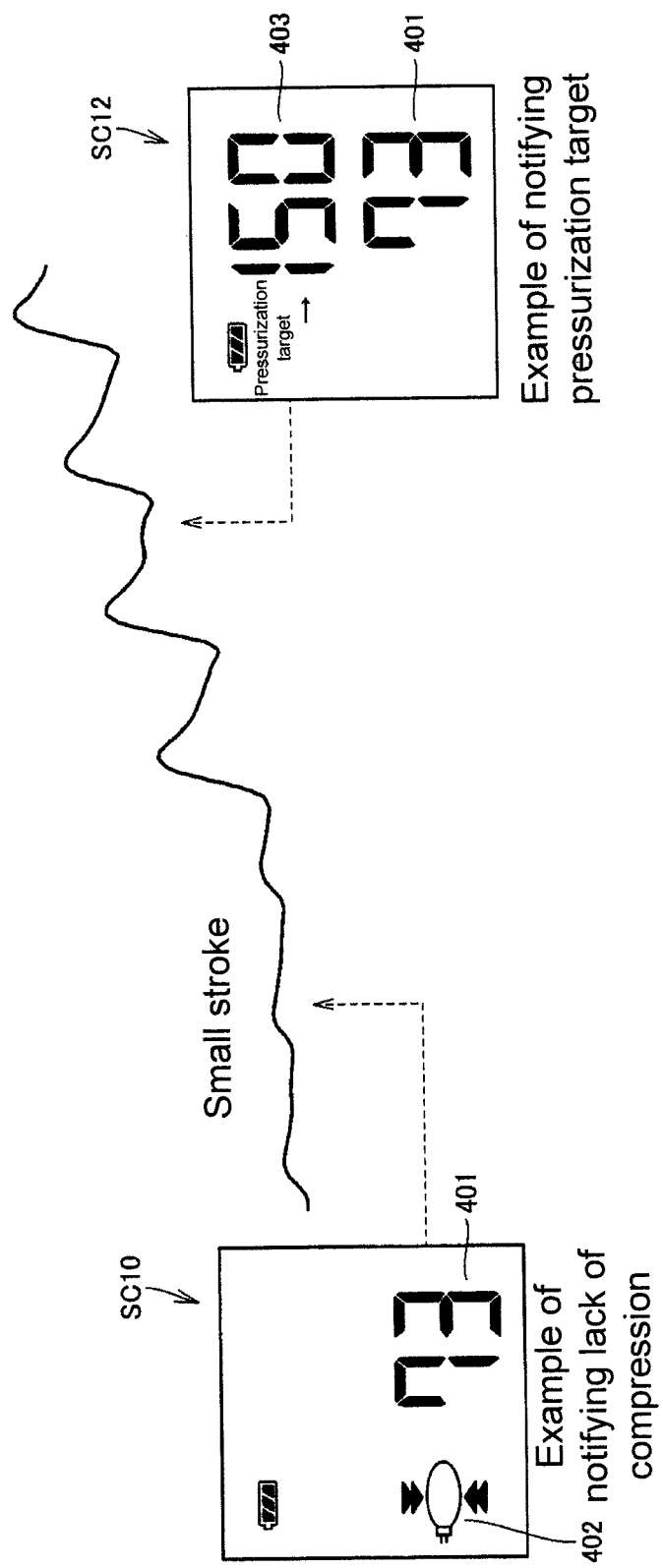
FIG. 14 is a diagram showing a display example of the lack of compression and the pressurization target value in the embodiment of the present invention.

FIG. 14 is a diagram showing a display example of the lack of compression and the pressurization target value in the embodiment of the present invention.

If it is determined that the stroke is small (manual amplitude is smaller than the threshold value Vb) after starting the blood pressure measurement process, the display control unit 112 displays a screen such as a screen SC10 of FIG. 14 (step S4). In the screen SC10, a current pressure value 401 and a predetermined mark 402 indicating lack of compression are displayed. The user is thus guided to make the stroke of the compressing operation larger.

In the present embodiment, the lack of compression is notified by the predetermined mark 402, but may be notified with a message. Alternatively, the lack of compression may be displayed in levels according to the difference between the manual amplitude and the threshold value Vb.

When the stroke becomes larger and the pressurization target value is derived, the display control unit 112 displays the screen such as a screen SC12 in FIG. 14. In the screen SC12, the current pressure value 401 and the pressurization target value 403 are displayed in contrast.

In the present embodiment, the current pressure value 401 and the pressurization target value 403 are displayed in contrast (in association), but are not limited to such an example as long as how much to pressurize can be recognized. For example, the display may be made with level etc. with the pressurization target value as 100% in a manner what percentage the current pressure value is can be recognized.

Furthermore, the pressurization target value is notified by display in the present embodiment, but this is not the sole case. For example, it may be notified with audio by the audio output unit (not shown) in place of/in addition to the display.

The pressurization is urged up to the pressurization target value by notifying the user at the time point the pressurization target value is calculated. However, the end of pressurization may be notified (display, alarm sound, audio, light, etc.) at the time point the current pressure value reached the pressurization target value in place of/in addition thereto. Even the visually impaired user thus can easily determine that the pressurization can be ended.

When guiding to large the scroll, this may be notified with audio or alarm sound in place of/in addition to the display. Alternatively, a beeping sound etc. may be output only when the manual amplitude becomes greater than or equal to the threshold value Vb so that the user can recognize appropriate compression.

In the present embodiment, the stroke of the manual operation is notified to be larger in order to avoid the manual pressurization component from being mistakenly recognized as a specific component. However, if the stroke is too large, the detected number of specific components reduces compared to when the stroke is small, as shown in the graphs of FIGS. 7(A) to 9(C). As described above, the systolic blood pressure can be estimated from one pulse wave amplitude value (amplitude value of pulse wave component), but the estimation accuracy is higher the greater the number of pulse wave amplitude values. Thus, the stroke may be notified to be made slightly smaller if the manual amplitude is greater than or equal to a predetermined threshold value Vc (value higher than the threshold value Vb). Alternatively, the current manual amplitude and the appropriate manual amplitude range (greater than or equal to threshold value Vb and smaller than threshold value Vc) may be displayed in a comparing manner so as to obtain an appropriate stroke range.

<Variant>

In the embodiment described above, the systolic blood pressure is estimated, and the value obtained by adding a predetermined value to the systolic blood pressure is notified as the final pressurization target value.

In the present variant, on the other hand, a value obtained by adding a predetermined value to a pressure value at a relevant time point every time the specific component is detected may be notified as the pressurization target value. That is, the pressurization target value is updated in the present variant.

Only the operation different from the embodiment described above will be described below.

In the present variant, only the process of the derivation processing unit 106 is different compared to the embodiment described above. Therefore, the derivation processing unit 106 will be described as a derivation processing unit 106A in the present variant.

Figure 15:
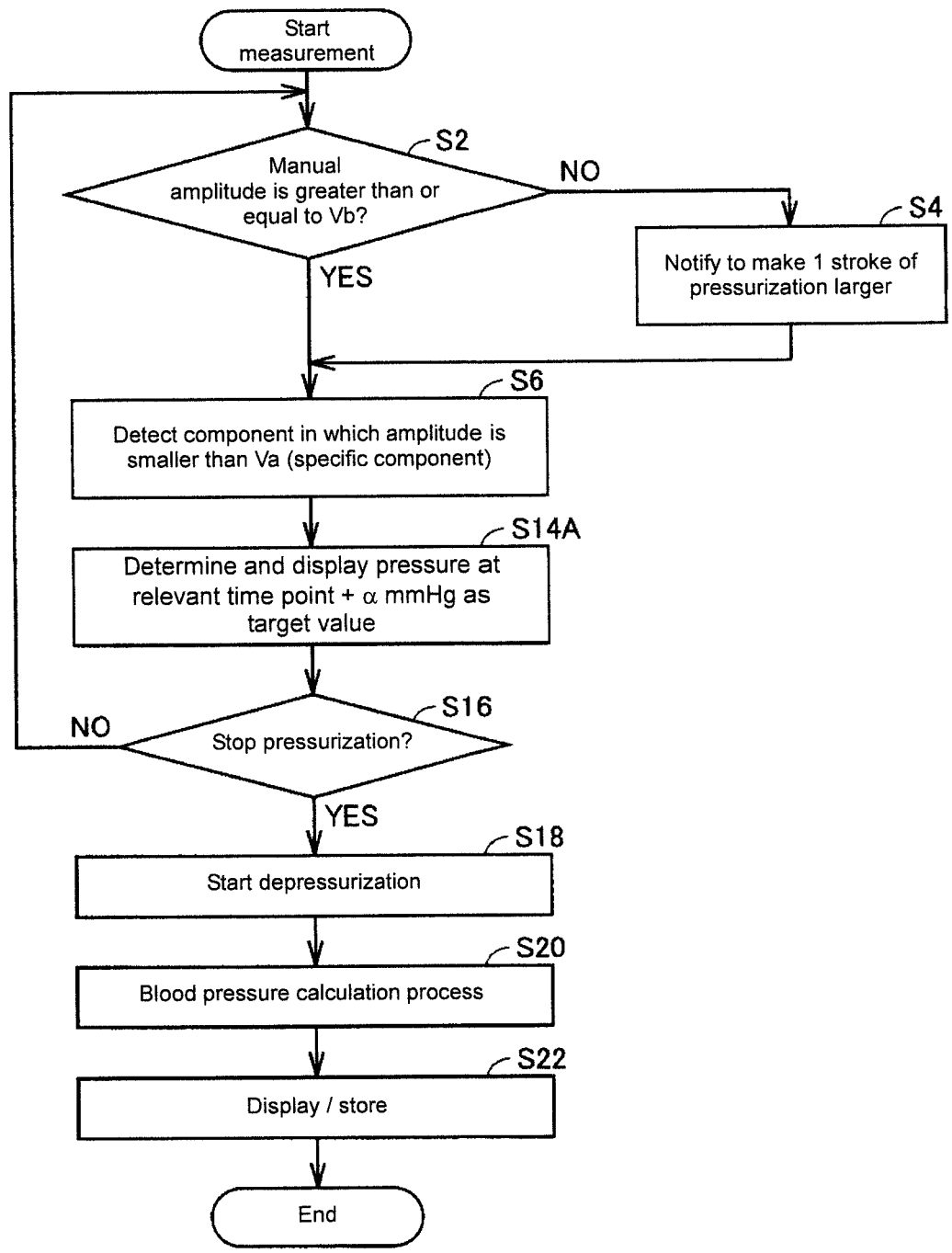
FIG. 15 is a flowchart showing the flow of a blood pressure measurement process according to a variant of the embodiment of the present invention.

FIG. 15 is a flowchart showing the flow of a blood pressure measurement process in the variant of the embodiment of the present invention. The same step number is denoted for the process similar to the flowchart of FIG. 12. Therefore, the description thereof will not be repeated.

With reference to FIG. 15, the process of step S14A is executed after the processes of steps S2 to S6 are finished without performing steps S8, S10.

In step S14A, the derivation processing unit 106A determines a value obtained by adding a predetermined value α (e.g., 40 mmHg) to the pressure value at the relevant time point as the pressurization target value. The display control unit 112 displays the determined pressurization target value in a predetermine display region of the display unit 40. The display example here may be similar to the screen SC12 of FIG. 14.

The "pressure value at the relevant time point" is the pressure value at the time point the specific component is detected, and may be a pressure value displayed as a current pressure value at the time point the specific component is detected (i.e., current pressure value detected by the pressure value detection unit 108). Alternatively, it may be a value within the pressure range of the specific component such as a maximal value or an average value of the detected specific component.

After the process of step S14A is finished, whether or not the pressurization is stopped is determined (step S16). If the pressurization is not stopped (NO in step S16), the process returns to step S2, and the above processes are repeated. The pressurization target value is thus updated and displayed every time the specific component is detected in step S6.

If the pressurization is stopped (YES in step S16), the processes (steps S18, S20, S22) similar to the above embodiment are executed.

Therefore, according to the present embodiment, the uses merely needs to continue pressurization until the current pressure value reaches the pressurization target value, although the pressurization target value is updated, and hence, pressurization can be carried out until ultimately reaching an appropriate value in a series of pressurizing operations in the present variant as well.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

Description of Reference Numerals
1 sphygmomanometer
10 main body
20 cuff
21 air bladder
24, 24A, 24B air tube
30 rubber bulb
31 exhaust port
32 pressure sensor
35 oscillation circuit
39 memory unit
40 display unit
41 operation unit
42 power supply unit
43 timing unit
44 beeper
100 CPU
102 determination unit
104 specific component detection unit
106, 106A derivation processing unit
108 pressure value detection unit
110 blood pressure calculation unit
112 display control unit
116 display unit

The invention claimed is:

1. A manual pressurization electronic sphygmomanometer comprising:
    a cuff to be wrapped around a predetermined body site;
    a manual pressurization unit that pressurizes a pressure in the cuff through a manual operation by a user;
    a pressure sensor that detects a cuff pressure signal representing the pressure in the cuff;
    a specific component detection unit that detects a synthetic wave of a manual fluctuation wave and a pressure pulse wave as a specific component from the cuff pressure signal obtained during the pressurization;
    a derivation processing unit that derives a pressurization target value based on the detection result of the specific component detection unit; and
    a notification unit that notifies to urge the pressurization up to the pressurization target value,
    wherein the derivation processing unit comprises:
        a first calculating portion that calculates an interpolation curve of the manual fluctuation wave for a portion of the specific component from waveforms before and after the specific component;
        a second calculating portion that calculates a pulse wave component by subtracting the interpolation curve from the specific component;
        an estimating portion that estimates a systolic blood pressure value based on an amplitude of the pulse wave component; and
        a determining portion that determines a value obtained by adding a predetermined value to the estimated systolic blood pressure value as the pressurization target value.

2. The electronic sphygmomanometer according to claim 1, further comprising:
    a pressure value detection unit that detects a current pressure value from the cuff pressure signal obtained during the pressurization,
    wherein the notification unit displays the current pressure value and the pressurization target value in association to each other.

3. The electronic sphygmomanometer according to claim 1, wherein the notification unit notifies an end of the pressurization when the current pressure value reaches the pressurization target value.

4. The electronic sphygmomanometer according to claim 1, wherein the specific component detection unit detects a pressure fluctuation component in which a pressure fluctuation component is smaller than a first threshold value in the cuff pressure signal obtained during the pressurization as the specific component.

5. The electronic sphygmomanometer according to claim 4, further comprising:
    a determination unit that determines whether or not a manual amplitude representing an amplitude of the manual fluctuation wave is greater than or equal to a second threshold value,
    wherein the second threshold value represents a value greater than or equal to the first threshold value, and
    wherein the notification unit further notifies to guide the user so that the manual amplitude becomes greater than or equal to the second threshold value when determined by the determination unit that the manual amplitude is smaller than the second threshold value.

* * * * *